(12) United States Patent
Segawa et al.

(10) Patent No.: US 10,306,908 B2
(45) Date of Patent: Jun. 4, 2019

(54) BACTERIAL STRAIN HAVING ANTI-ALLERGIC ACTIVITY, AND BEVERAGE, FOOD AND ANTI-ALLERGIC AGENT COMPRISING CELL OF THE BACTERIAL STRAIN

(71) Applicant: SAPPORO HOLDINGS LIMITED, Shibuya-ku (JP)

(72) Inventors: Syuichi Segawa, Shibuya-ku (JP); Yasukazu Nakakita, Shibuya-ku (JP); Yoshihiro Takata, Yokohama (JP); Hisako Yasui, Kamiina-gun (JP)

(73) Assignee: Sapporo Holdings Limited, Tokyo (JP)

( * ) Notice: Subject to any disclaimer, the term of this patent is extended or adjusted under 35 U.S.C. 154(b) by 447 days.

(21) Appl. No.: 14/682,383

(22) Filed: Apr. 9, 2015

(65) Prior Publication Data
US 2015/0208709 A1  Jul. 30, 2015

Related U.S. Application Data

(62) Division of application No. 12/438,411, filed as application No. PCT/JP2007/066121 on Aug. 20, 2007, now abandoned.

(30) Foreign Application Priority Data

Aug. 21, 2006  (JP) ................................ 2006-224765

(51) Int. Cl.
| A61K 35/747 | (2015.01) |
| A23L 33/135 | (2016.01) |
| A23L 2/40 | (2006.01) |
| A23L 2/52 | (2006.01) |
| C12C 12/00 | (2006.01) |
| C12N 1/20 | (2006.01) |
| C12P 7/52 | (2006.01) |
| C12P 13/00 | (2006.01) |
| C12R 1/24 | (2006.01) |
| A61K 35/00 | (2006.01) |

(52) U.S. Cl.
CPC ............... *A23L 33/135* (2016.08); *A23L 2/40* (2013.01); *A23L 2/52* (2013.01); *A61K 35/747* (2013.01); *C12C 12/008* (2013.01); *C12N 1/20* (2013.01); *C12P 7/52* (2013.01); *C12P 13/005* (2013.01); *C12R 1/24* (2013.01); *A23V 2002/00* (2013.01); *A23Y 2220/13* (2013.01); *A61K 2035/115* (2013.01)

(58) Field of Classification Search
CPC ............... A23V 2250/038; A23V 2200/3204
See application file for complete search history.

(56) References Cited

U.S. PATENT DOCUMENTS

| 5,556,785 A | 9/1996 | Kishida |
| 2005/0238693 A1* | 10/2005 | Whyte ................ A61K 31/00 424/439 |
| 2006/0083723 A1 | 4/2006 | Ching-Hsiang et al. |

FOREIGN PATENT DOCUMENTS

| JP | 6 206826 | 7/1994 |
| JP | 9 2959 | 1/1997 |
| JP | 10 309178 | 11/1998 |
| JP | 2000 95697 | 4/2000 |
| JP | 2005 139160 | 6/2005 |

OTHER PUBLICATIONS

JP09-002959, 1997, English Machine Translation from J-PlatPat, pp. 1-7.*
Tsuchiya, Youichi et al., "Monoclonal Antibodies Specific for the Beer-Spoilage Ability of Lactic Acid Bacteria", J. Am. Soc. Brew. Chem., Vo.. 58, No. 3, pp. 89-93 (2000).
Takahashi, Toshihiro, et al., "Classification and Identification of Strains of Lactobacillus brevis Based on Electrophoretic Characterization of D-Lactate Dehydrogenase: relationship between D-Lactate Dehydrogenase and Beer-Spoilage Ability", Journal of Bioscience and Bioengineering, vol. 88, No. 5, pp. 500-506 (1999).
Kishi, Atsuko et al., "Effect of the oral Administration of *Lactobacillus brevis* subsp. Coagulans on Interferon-alpha Producing Capacity in Humans", Journal of the American College of Nutrition, vol. 15, No. 4, pp. 408-412, (1996).
Yokoyama, Sadaji, et al., "Production of γ-Aminobutyric Acid from Alcohol Distillery Lees by Lactobacillus brevis IFO-12005", Journal of Bioscience and Bioengineering, vol. 93, No. 1, pp. 95-97, (2002).
Yajima, Nobuhiko, et al., "Characteristics of Lactobacillus brevis and its physiological function", Milk Science, vol. 55, No. 2, pp. 89-90, (2005), (with partial translation).
Ogino, Satoshi "Stress and Allergic diseases, Survey of Preparatory School Students", OTO-Rhino-Laryngology, vol. 45, No. 3, pp. 187-188 and 204-210, (2002), (with English Translation).
Extended European Search Report dated Jan. 3, 2011, in European Patent Application No. 07792734.1.
International Search Report dated Sep. 11, 2007 in PCT/JP07/66121 Filed Aug. 20, 2007.

* cited by examiner

*Primary Examiner* — Julie Wu
*Assistant Examiner* — Douglas F White
(74) *Attorney, Agent, or Firm* — Morgan, Lewis & Bockius LLP

(57) ABSTRACT

It is an object of the present invention to provide a bacterial strain belonging to *Lactobacillus brevis* subspecies *brevis*, which has more potent antiallergic activity than the known lactic acid bacteria strains and produces γ-aminobutyric acid (GABA). It is another object of the present invention to provide beverages and foods containing cells of the aforementioned bacterial strain belonging to *Lactobacillus brevis* subspecies *brevis*, as well as antiallergic agents containing them as an active ingredient. The present invention provides a bacterial strain belonging to *Lactobacillus brevis* subspecies *brevis*, which: is capable of growing in effervescent alcoholic beverages, produces γ-aminobutyric acid (GABA), and has antiallergic activity.

12 Claims, 12 Drawing Sheets

BACTERIAL STRAIN HAVING ANTI-ALLERGIC ACTIVITY, AND BEVERAGE, FOOD AND ANTI-ALLERGIC AGENT COMPRISING CELL OF THE BACTERIAL STRAIN

The present application is a divisional application of U.S. application Ser. No. 12/438,411 filed May 14, 2009, pending, that is a National Stage of PCT/JP07/66121 filed Aug. 20, 2007 and claims the benefit of JP 2006-224765 filed Aug. 21, 2006.

TECHNICAL FIELD

The present invention relates to a bacterial strain with antiallergic activity, and to beverages, foods and antiallergic agents containing cells thereof.

BACKGROUND ART

Allergic diseases are commonly treated by drug therapy with an antihistamine, antiallergic, steroid or the like. Recently, however, in light of the limits of drug therapy and from the viewpoint of preventive medicine, lactic acid bacteria affecting gut immunity have attracted attention for their effectiveness in the prevention and treatment of allergic diseases (Patent documents 1 to 3). Gut immunity is an immune mechanism for elimination of pathogenic microorganisms that have been orally ingested, and it is the current opinion that suppression of overresponse of the gut immunity is useful in the prevention and treatment of allergic diseases.

For example, it has been reported that some strains of *Bifidobacterium infantis, Bifidobacterium breve, Bifidobacterium longum* and *Bifidobacterium bifidum* are effective in the treatment of food allergy (Patent document 1). Also, it has been reported that some strains of *Enterococcus faecalis, Lactobacillus reuteri* (Patent document 2), *Lactobacillus paracasei, Lactobacillus plantarum* and *Streptococcus salivarius* (Patent document 3) are effective against bronchial asthma, allergic rhinitis and atopic dermatitis.

Further, it is known that allergic diseases correlate with physical and psychological stress, and that individuals with higher stress levels exhibit worse symptoms (Non-patent document 1). It is therefore believed that not only suppression of the immune response of the body but also elimination of daily stress is required to prevent and treat allergic diseases.

Patent document 1: Japanese Patent Application Laid-Open No. 10-309178
Patent document 2: Japanese Patent Application Laid-Open No. 2000-95697
Patent document 3: Japanese Patent Application Laid-Open No. 2005-139160
Non-patent document 1: Satoshi Ogino, "Stress and Allergic Diseases: Focus on Preparatory School Students", Jibiinkoka Tenbo (Oto-rhino-laryngology, Tokyo), 2002, Vol. 45, p. 204-210

DISCLOSURE OF THE INVENTION

Problem to be Solved by the Invention

Drug therapy with an antihistamine, antiallergic, steroid or the like can produce serious side-effects, because it directly affects molecules involved in the immune response in the blood and suppresses immune responses essential for maintaining homeostasis. Also, from a practical standpoint, the efficacy of the hitherto-reported lactic acid bacteria is insufficient for the prevention of chronic diseases such as allergic diseases. Further, as of the current writing, no reports exist of a lactic acid bacteria strain that produces γ-aminobutyric acid (GABA), which has antiallergic activity and anti-stress activity.

It is an object of the present invention to provide a bacterial strain belonging to *Lactobacillus brevis* subspecies *brevis*, which has more potent antiallergic activity than the known lactic acid bacteria strains and produces γ-aminobutyric acid (GABA). It is another object of the present invention to provide beverages and foods containing cells of the aforementioned bacterial strain belonging to *Lactobacillus brevis* subspecies *brevis*, as well as antiallergic agents containing them as an active ingredient.

Means for Solving the Problem

In order to achieve the object stated above, the present invention provides a bacterial strain belonging to *Lactobacillus brevis* subspecies *brevis*, which strain is capable of growing in effervescent alcoholic beverages, produces γ-aminobutyric acid (GABA) and has antiallergic activity.

The present inventors have discovered that among lactic acid bacteria of *Lactobacillus brevis*, bacterial strains belonging to the subspecies *brevis*, in particular, effectively induce the production of Th1 cytokines by mouse spleen cells and inhibit the production of IgE. These activities are effective for the prevention and treatment of human allergic diseases, and are notably potent compared to the hitherto-reported lactic acid bacteria strains. Lactic acid bacteria have been conventionally used in fermented food products and are far safer for the human body than chemically synthesized antiallergic drugs. Ordinary lactic acid bacteria cannot grow in effervescent alcoholic beverages, while the bacterial strain of the invention is capable of growing in effervescent alcoholic beverages. This property can be utilized to separate the bacterial strain of the invention from other lactic acid bacteria strains with no antiallergic activity. Also, since the bacterial strain of the invention produces γ-aminobutyric acid (GABA), it has anti-stress activity as well as antiallergic activity, and is therefore expected to have a robust, multifaceted effect in the prevention and treatment of allergic diseases which correlate with physical and psychological stress. A particularly preferred example of such a bacterial strain is *Lactobacillus brevis* subspecies *brevis* SBC8803 (FERM BP-10632).

The antiallergic activity is preferably activity which promotes interferon γ and/or interleukin 12 production.

Interferon γ is a cytokine secreted by Th1 cells. As well as inhibiting the production of IgE by B cells, it enhances the cell-mediated immunity of killer T cells, macrophages and the like, which attack viruses, filamentous fungi, tubercle bacilli, etc. Interleukin 12 is a cytokine secreted by antigen-presenting cells such as macrophages. It stimulates NK cells and induces Th1 cells, and further induces the production of interferon γ by Th1 cells. Since the bacterial strain of the invention promotes the production of interferon γ and/or interleukin 12 and inhibits the production of IgE, it can inhibit type I allergic reaction.

The antiallergic activity is preferably activity which inhibits IgE production.

IgE is a substance which causes allergic diseases. Specifically, IgE is produced in response to invasion by allergens, and binds to mast cells or basophils to establish sensitization. Upon subsequent exposure to the same allergen, IgE recognizes the allergen and causes release of inflammatory substances such as histamines from mast cells or basophils. This allergic reaction is responsible for various symptoms including bronchial constriction and urticaria, and leads to allergic diseases, such as pollen hypersensitivity, allergic rhinitis, atopic dermatitis and asthma, depending on the site of onset. Since the bacterial strain of the invention inhibits the production of IgE, it can inhibit allergic reaction and can thus be used for the prevention and treatment of such allergic diseases.

The present invention further provides beverages and foods containing cells of the aforementioned bacterial strain.

Since cells of the aforementioned bacterial strain have antiallergic activity and are safe for the human body, they can be used as a health food ingredient in beverages and foods. In addition, since the aforementioned bacterial strain produces γ-aminobutyric acid (GABA), they have anti-stress activity, hypotensive activity and tranquilizing property, and are therefore highly useful as a health food ingredient.

The present invention still further provides antiallergic agents containing cells of the aforementioned bacterial strain as an active ingredient.

Since cells of the aforementioned bacterial strain promote the production of interleukin 12 and interferon γ and inhibit the production of IgE, antiallergic agents containing them as an active ingredient can be utilized as antiallergic agents that are safer than chemically synthesized drugs.

Effects of the Invention

The present invention provides a bacterial strain belonging to *Lactobacillus brevis* subspecies *brevis*, which has more potent antiallergic activity than hitherto-known lactic acid bacteria strains. The bacterial strain of the invention is capable of growing in effervescent alcoholic beverages, and this property can be utilized to separate the bacterial strain of the invention from other lactic acid bacteria strains with no antiallergic activity. Also, since the bacterial strain of the invention produces γ-aminobutyric acid (GABA), it has anti-stress activity as well as antiallergic activity, and is therefore expected to have a robust effect in the prevention and treatment of allergic diseases which correlate with physical and psychological stress. The present invention further provides highly safe beverages, foods and antiallergic agents which contain cells of the aforementioned bacterial strain and have antiallergic activity.

BEST MODES FOR CARRYING OUT THE INVENTION

Figure 1:
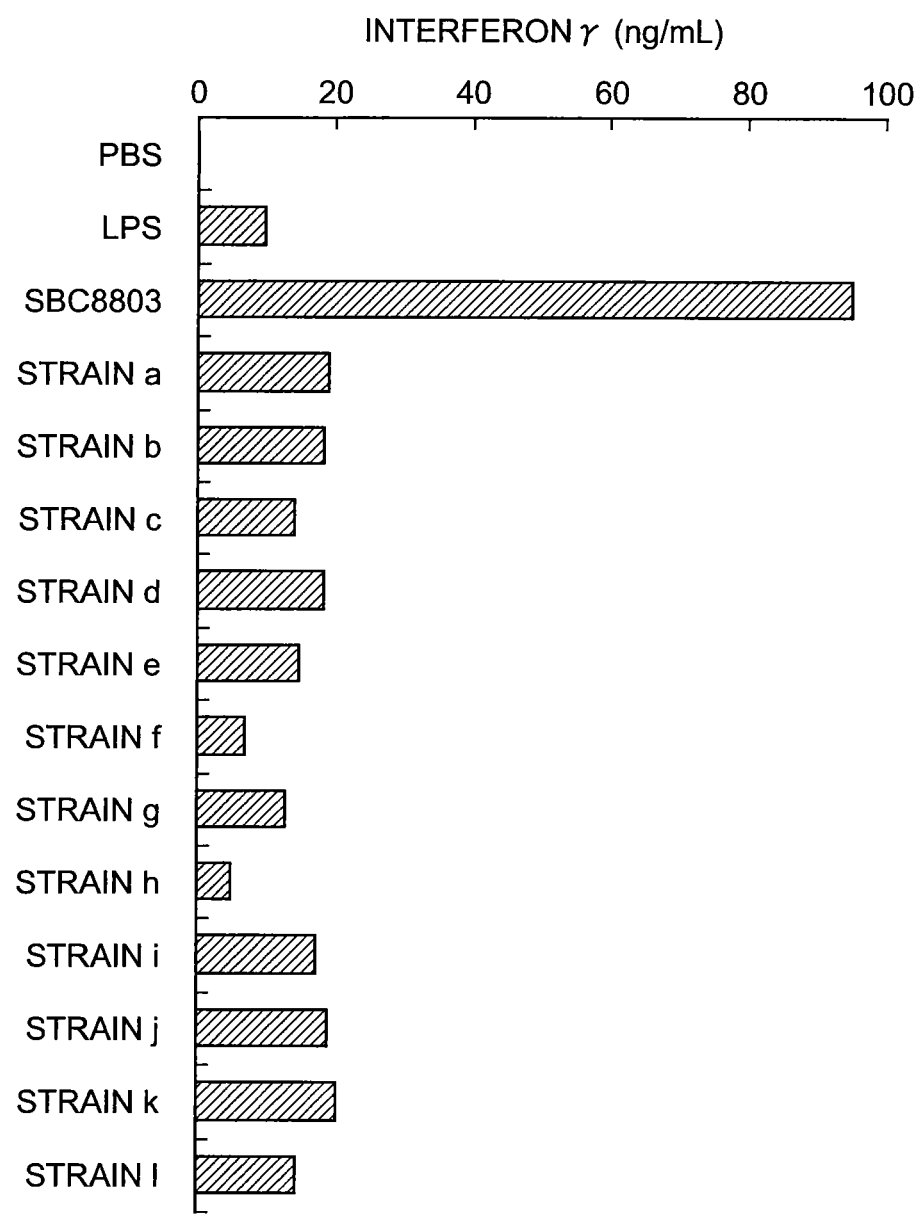
FIG. 1 shows the amount of interferon γ produced by mouse spleen cells upon addition of a cell suspension of each of bacterial strains belonging to *Lactobacillus brevis* subspecies *brevis*.

Preferred embodiments of the present invention will now be described in detail.

The bacterial strain of the invention is a bacterial strain belonging to *Lactobacillus brevis* subspecies *brevis*, which strain is capable of growing in effervescent alcoholic beverages, produces γ-aminobutyric acid (GABA) and has antiallergic activity.

*Lactobacillus brevis* consists of the following four subspecies: *brevis, gravesensis, otakiensis* and *coagulans*. The aforementioned bacterial strain belongs to the subspecies *brevis*. Bacterial strains belonging to the subspecies *brevis* can be separated based on, for example, their 16S ribosomal DNA nucleotide sequences and differences in production of acids from sugars, and can be classified as bacterial strains not belonging to the subspecies *gravesensis*, subspecies *otakiensis* or subspecies *coagulans*.

The "antiallergic activity" means activity which inhibits allergic reaction. The "allergy" refers to a condition in which antibodies have been produced in the body as a result of ingestion of, or contact with, a certain substance, and subsequent ingestion of, or contact with, the same substance provokes an excessive antigen-antibody reaction which causes a pathological symptom. The "allergic reaction" means a phenomenon wherein an immune response, which is a defense mechanism of the body, causes an attack on the body's own cells or ingested food, which should not be eliminated. An immune response involves antigen-presenting cells, T cells and B cells, and mainly IgG and IgA are produced in a humoral immune response. However, an allergic reaction involves primarily Th2 cells, and IgE is produced at a concentration 100 to 10,000 times higher than in an ordinary immune response. This abundant IgE binds to mast cells and stimulates release of inflammatory substances such as histamines and leukotrienes from the mast cells.

Examples of the antiallergic activity are: activity on antigen-presenting cells, T cells or mast cells, which activity inhibits the production of IgE or the release of the aforementioned inflammatory substances; and activity which causes a shift of the Th1/Th2 balance toward Th1. More specifically, examples are: activity which inhibits IgE production; and activity which promotes interferon γ and interleukin 12 production.

The antiallergic activity of the aforementioned bacterial strain is preferably activity which inhibits IgE production, activity which promotes interferon γ production, and/or activity which promotes interleukin 12 production, and more preferably, the bacterial strain has two or more of these activities.

Examples of the "effervescent alcoholic beverage" are beer, low-malt beer (happoshu), and other types of alcoholic beverages. Being "capable of growing in effervescent alcoholic beverages" means that the lactic acid bacteria are not killed in effervescent alcoholic beverages, and they undergo cell division to increase their cell number. The alcohol concentration of the effervescent alcoholic beverages is preferably at least 5%.

Bacterial strains belonging to *Lactobacillus brevis* subspecies *brevis* can be easily isolated from nature, and can be identified by examining their 16S ribosomal DNA nucleotide sequences. They can also be purchased from cell banks such as ATCC.

Bacterial strains belonging to *Lactobacillus brevis* subspecies *brevis* which are capable of growing in effervescent alcoholic beverages can be selected out by the method described in Japanese Patent Application Laid-Open No. 2003-250557. Specifically, the screening can be carried out as follows. PCR is performed on genomic DNA of bacterial strains belonging to *Lactobacillus brevis* subspecies *brevis* using a prescribed primer set and the amplified DNA gyrase subunit B gene fragments are cut with a restriction enzyme. The restriction enzyme cleavage patterns are analyzed after acrylamide gel electrophoresis, and bacterial strains belonging to group IIb are selected out. Restriction enzyme cleavage patterns fall roughly into 4 groups, and the bacterial strains capable of growing in effervescent alcoholic beverages have been known to belong to group IIb.

Such bacterial strains can also be selected out by inoculating bacterial strains belonging to *Lactobacillus brevis* subspecies *brevis* in an effervescent alcoholic beverage, culturing them, and determining whether they can grow or not. Although 30° C. is more suitable, the cultivation temperature may be 15° C. to 45° C. and is preferably 20° C. to 37° C., especially around 30° C.

Bacterial strains belonging to *Lactobacillus brevis* subspecies *brevis* which produce γ-aminobutyric acid (GABA) can be selected out by analyzing culture supernatants with an amino acid analyzer or the like and determining the GABA contents.

Bacterial strains belonging to *Lactobacillus brevis* subspecies *brevis* which have antiallergic activity can be selected out by examining whether or not bacterial strains have, for example, i) activity which promotes interferon γ and interleukin 12 production by mouse spleen cells, ii) activity which inhibits IgE production induced in spleen cells of ovalbumin (OVA)-immunized mice, or iii) activity which inhibits the production of IgE secreted into the peripheral blood of OVA-immunized mice.

As for i), the presence or absence of activity which promotes interferon γ and interleukin 12 production can be determined as follows. Spleen cells are extracted from mouse spleens and cultured. A cell suspension prepared by sterilizing cells of the test strain is added thereto, and the mixture is cultured for a prescribed period of time. Then, the amounts of interferon γ and interleukin 12 secreted from the spleen cells are measured by ELISA or the like.

As for ii), the presence or absence of activity which inhibits IgE production can be determined as follows. Spleen cells are extracted from OVA-immunized mice 2 weeks after booster immunization and cultured. A cell suspension prepared by sterilizing cells of the test strain and OVA are added thereto, and the mixture is cultured for a prescribed period of time. Then, the amount of IgE secreted from the spleen cells is measured by ELISA or the like.

As for iii), the examination can be carried out as follows. A cell suspension prepared by sterilizing cells of the test strain is administered intraperitoneally to OVA mice, and the mice are raised for a prescribed period of time. Then, the amount of IgE secreted into the peripheral blood is measured by ELISA or the like, and this is compared with the amount of IgE secreted into the peripheral blood of OVA mice which have not received intraperitoneal administration of the cell suspension.

The strain SBC8803 belonging to *Lactobacillus brevis* subspecies *brevis*, which is capable of growing in effervescent alcoholic beverages, produces GABA, and has antiallergic activity, was deposited with the International Patent Organism Depositary, National Institute of Advanced Industrial Science and Technology (Tsukuba Central 6, 1-1, Higashi 1-chome Tsukuba-shi, Ibaraki-ken 305-8566 Japan), an international depositary authority, on Jun. 28, 2006 under accession number FERM BP-10632, and is available.

The beverage, food and antiallergic agent of the invention contains the aforementioned bacterial strain belonging to *Lactobacillus brevis* subspecies *brevis*, which is capable of growing in effervescent alcoholic beverages, produces GABA, and has antiallergic activity.

Cells of the aforementioned bacterial strain can be added to beverages and foods with a view to preventing or treating allergic diseases. Such beverages and foods may consist entirely of the bacterial cells, or may contain additives commonly used in the relative field. As examples of such additives, there may be mentioned, for example, apple fiber, soybean fiber, meat extract, black vinegar extract, gelatin, corn starch, honey, animal and vegetable oil and fat, monosaccharides such as glucose, disaccharides such as sucrose, fructose and mannitol, polysaccharides such as dextrose and starch, sugar alcohols such as erythritol, xylitol and sorbitol, vitamins such as vitamin C, and the like. These additives may be used alone or in combinations.

They may also be blended as food additives into various types of beverages and foods, such as special health foods, special nutritional foods, nutritional supplements, health foods, functional foods and patient foods, with a view to preventing, or alleviating the symptoms of, allergic diseases.

The antiallergic agent of the invention contains cells of the aforementioned bacterial strain as an active ingredient, and if it is formulated with the addition of a carrier, excipient and/or other additives, it can be used as a highly safe antiallergic agent. As examples of pharmaceutically acceptable additives, there may be mentioned, for example, monosaccharides such as glucose, disaccharides such as sucrose, fructose and mannitol, polysaccharides such as dextrose and starch, sugar alcohols such as erythritol, xylitol and sorbitol, vitamins such as vitamin C, acacia gum, calcium phosphate, alginates, calcium silicate, microcrystalline cellulose, polyvinylpyrrolidone, cellulose derivatives, tragacanth, gelatin, syrups, methyl hydroxybenzoate, talc, magnesium stearate, water, mineral oils, and the like. These additives may be used alone or in combinations.

EXAMPLES

The present invention will now be explained in greater detail with reference to examples, with the understanding that the invention is not meant to be limited to these examples.

1) Bacterial Strains Used for Experiments

Thirteen bacterial strains belonging to *Lactobacillus brevis* subspecies *brevis* (SBC8803 and strains a to 1) were separated by the present inventors and stored at 4° C. as lyophilized cells until use in the experiment. Strain X belonging to *Lactobacillus rhamnosus* was separated from commercially available yogurt and stored at 4° C. as lyophilized cells until use in the experiment.

2) Determination of Growth Ability in Beer

The 13 bacterial strains belonging to *Lactobacillus brevis* subspecies *brevis* and strain X belonging to *Lactobacillus rhamnosus* were screened for ability to grow in beer. The screening was carried out in the manner described in Japanese Patent Application Laid-Open No. 2003-250557. Specifically, PCR was performed on the genomic DNA of each lactic acid bacteria strain using a prescribed primer set. The amplified DNA gyrase subunit B gene fragment was cut with a restriction enzyme, and the restriction enzyme cleavage pattern was analyzed after acrylamide gel electrophoresis. In this method, restriction enzyme cleavage patterns fall roughly into 4 groups, and the bacterial strains capable of growing in beer have been known to belong to group IIb.

The 13 bacterial strains belonging to *Lactobacillus brevis* subspecies *brevis* were all determined to be capable of growing in beer, whereas strain X belonging to *Lactobacillus rhamnosus* was not determined to be capable of growing in beer. Then, these bacterial strains were actually inoculated into beer to confirm whether or not they were capable of growing in beer, and the same results were obtained.

3) Evaluation of Antiallergic Activity i) Preparation of Cell Suspensions

A cell suspension of each of the aforementioned bacterial strains was prepared to evaluate their antiallergic activities. First, each bacterial strain was cultured statically in MRS broth (Difco) (composition: 1% proteose peptone, 1% beef extract, 0.5% yeast extract, 2% glucose, 0.1% Tween 80, 0.5% ammonium citrate, 0.01% magnesium sulfate, 0.005% manganese sulfate, 0.2% dipotassium phosphate) for 3 days under an anaerobic condition ($N_2$—$CO_2$—$H_2$ (90:5:5) gas). Then, the culture solution was centrifuged at 1500 rpm for 10 minutes, and cells of each strain were recovered. The obtained cells were washed with PBS, lyophilized, and suspended in PBS to a final concentration of 1 mg/mL. The cell suspensions thus obtained were subjected to autoclave sterilization (121° C., 15 min) and used in the following experiment.

ii) Interferon γ Production-Promoting Effect of Bacterial Strains Belonging to *Lactobacillus brevis* Subspecies *Brevis* on Mouse Spleen Cells (In Vitro)

The interferon γ production-promoting effects of the 13 bacterial strains belonging to *Lactobacillus brevis* subspecies *brevis* were evaluated by addind a cell suspension of each bacterial strain to mouse spleen cells, culturing the mixture for a prescribed period of time, and measuring the amount of interferon γ secreted from the spleen cells.

(Preparation of Mouse Spleen Cells)

First, spleens were aseptically extracted from 6-week-old BALB/c mice (female) and immersed in RPMI 1640 medium containing 10% FBS. The spleens were then transferred to a dish and ground with a pestle, and the mouse spleen cell suspension was passed through a nylon filter net with an opening size of 70 μm and wire diameter of 39 μm (Nippon Rikagaku Kikai). The mouse spleen cell suspension that had passed through the nylon filter net was centrifuged at 1500 rpm for 10 minutes. After discarding the supernatant, a hemolysis reagent (0.16 M ammonium chloride, Tris-HCl, pH 7.2) was added to the precipitated mouse spleen cells, and the mixture was allowed to stand for 5 minutes at room temperature. Then, fresh RPMI 1640 medium containing 10% FBS was added to wash the mouse spleen cells, and the mixture was centrifuged at 1500 rpm for 10 minutes. After discarding the supernatant, RPMI 1640 medium containing 10% FBS was added to bring the cell concentration to $5 \times 10^6$ cells/mL. The mouse spleen cells thus obtained were used in the following experiment.

(Measurement of Interferon γ by ELISA)

The mouse spleen cells were seeded in a 96-well plate at a density of $2.5 \times 10^6$ cells/mL, and cultured in RPMI 1640 medium containing 10% FBS under conditions of 37° C., 5% $CO_2$. A cell suspension of each bacterial strain (final concentration: 10 μg/mL) was added to each well in which the mouse spleen cells were being cultured. After 72 hours, interferon γ secreted into the culture supernatant was quantified by ELISA. Lipopolysaccharide (LPS) (Sigma), which exhibits an interferon γ production-promoting effect on mouse spleen cells, was used at a final concentration of 10 μg/mL as a positive control, and PBS was used as a negative control.

Quantification of interferon γ by ELISA was carried out as follows. First, 50 μL of a primary antibody (rabbit anti-mouse/rat interferon-γ, BioSource) prepared to 1.25 μg/mL was added to each well of a 96-well plate (Maxisorp Immunoplate, Nunk), and the mixture was allowed to stand overnight at 4° C. for fixation. Then, the 96-well plate was washed 3 times with wash buffer and subjected to blocking with 1% bovine serum albumin (BSA) (Sigma). Next, 50 μL of each culture supernatant or an interferon γ standard with a known concentration of interferon γ was added to each well and allowed to react with the anti-interferon γ primary antibody for 90 minutes. After washing 3 times with wash buffer, 50 μL of a secondary antibody (anti-mouse/rat interferon γ biotin conjugate, BioSource) prepared to 0.5 μg/mL was added to each well and allowed to react at room temperature for 90 minutes. Then, each well was washed 5 times with wash buffer, and streptavidin-HRP (BioSource) was added and allowed to react. After washing another 5 times with wash buffer, a TMB (tetramethylbenzidine) substrate solution (3,3',5,5'-Tetramethylbenzidine (TMB) Liquid Substrate System, Sigma) was added and allowed to react. After sufficient color development, 50 μL of 2N sulfuric acid was added to each well to terminate the reaction, and the absorbance at 450 nm was measured. A standard curve was prepared from the absorbances of the interferon γ standards, and interferon γ produced by the mouse spleen cells was quantified using the standard curve.

FIG. 1 shows the amount of interferon γ produced by mouse spleen cells upon addition of a cell suspension of each of the 13 bacterial strains belonging to *Lactobacillus brevis* subspecies *brevis*. SBC8803 belonging to *Lactobacillus brevis* subspecies *brevis* induced interferon γ production by mouse spleen cells, and the amount produced was significantly greater compared to LPS and the other bacterial strains belonging to *Lactobacillus brevis* subspecies *brevis* (strains a to 1). The strain SBC8803, which exhibited interferon γ production-inducing activity, was deposited with the International Patent Organism Depositary, National Institute of Advanced Industrial Science and Technology (Tsukuba Central 6, 1-1, Higashi 1-chome Tsukuba-shi, Ibaraki-ken 305-8566 Japan), an international depositary authority, on Jun. 28, 2006 under accession number FERM BP-10632.

iii) Th1 Cytokine Production-Promoting Effect, Th2 Cytokine Production-Inhibiting Effect and IgE Production-Inhibiting Effect of SBC8803 on Spleen Cells of OVA-Immunized Mice (In Vitro)

SBC8803, which had exhibited an interferon γ production-promoting effect on mouse spleen cells, was evaluated with respect to its Th1 cytokine (interferon γ and interleukin 12) production-promoting effect, Th2 cytokine (interleukin 4) production-inhibiting effect and IgE production-inhibiting effect on spleen cells of OVA-immunized mice. Also, strains b and c belonging to Lactobacillus brevis subspecies brevis and strain X belonging to Lactobacillus rhamnosus were examined in the same manner and compared with SBC8803.

(Preparation of OVA-Immunized Mice)

OVA-immunized mice were prepared by intraperitoneally administering OVA to 6-week-old BALB/c mice (female) to induce allergy. Specifically, an OVA antigen solution was prepared by dissolving 100 μg of OVA (ovalbumin, egg-white, purified; Worthington Biochemical) and 10 mg of aluminum hydroxide in 1 mL of PBS, and 200 μL thereof was administered intraperitoneally to the mice as a primary immunization. After one week, an OVA antigen solution was prepared in the same manner as described above, and 200 μL thereof was administered intraperitoneally to the mice as a booster immunization. Allergy occurred in the boosted mice after about one week, and these mice were used as OVA-immunized mice in the following experiment.

(Preparation of Spleen Cells of OVA-Immunized Mice)

Two weeks after the booster immunization, spleens were aseptically extracted from the OVA-immunized mice, and spleen cells were prepared by the same procedure as described above.

(Measurement of Interferon γ, Interleukin 12 and Interleukin 4 by ELISA)

$2.5 \times 10^5$ spleen cells of OVA-immunized mice were seeded in a 96-well plate (cell density: $2.5 \times 10^6$ cells/mL), and cultured in RPMI 1640 medium containing 10% FBS under conditions of 37° C., 5% $CO_2$. OVA (final concentration: 100 μg/mL) and a cell suspension of each bacterial strain (final concentration: 1 μg/mL) were added to each well in which the spleen cells of OVA-immunized mice were being cultured. After 72 hours, each of the cytokines secreted into the culture supernatant was quantified by ELISA. As a control, PBS was added instead of the cell suspension.

Quantification of interferon γ by ELISA was carried out in the same manner as described above. As for quantification of interleukin 12, ELISA was performed by the same procedure as used for the quantification of interferon γ, except that 1 μg/mL of purified anti-mouse IL-12 (p40/p70) (BD Pharmingen) was used as the primary antibody and 1 μg/mL of biotinylated anti-mouse IL-12 (p40/p70) (BD Pharmingen) was used as the secondary antibody. As for quantification of interleukin 4, ELISA was performed by the same procedure as used for the quantification of interferon γ, except that 1 μg/mL of monoclonal anti-mouse IL-4 antibody (R&D Systems) was used as the primary antibody and 1 μg/mL of biotinylated anti-mouse IL-4 antibody (R&D Systems) was used as the secondary antibody.

Figure 2:
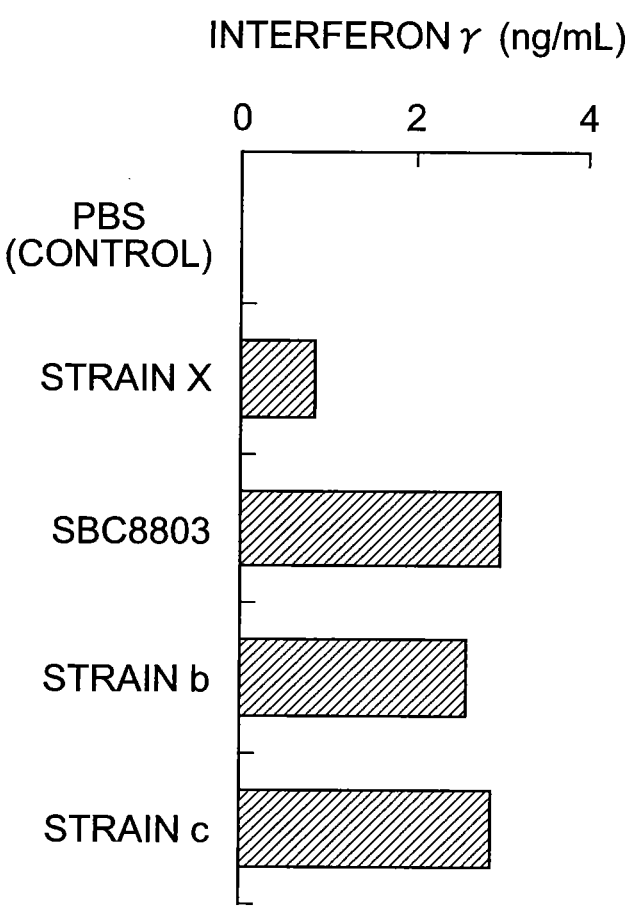
FIG. 2 shows the amount of interferon γ produced by spleen cells of OVA-immunized mice upon addition of OVA and a cell suspension of each of bacterial strains.
Figure 3:
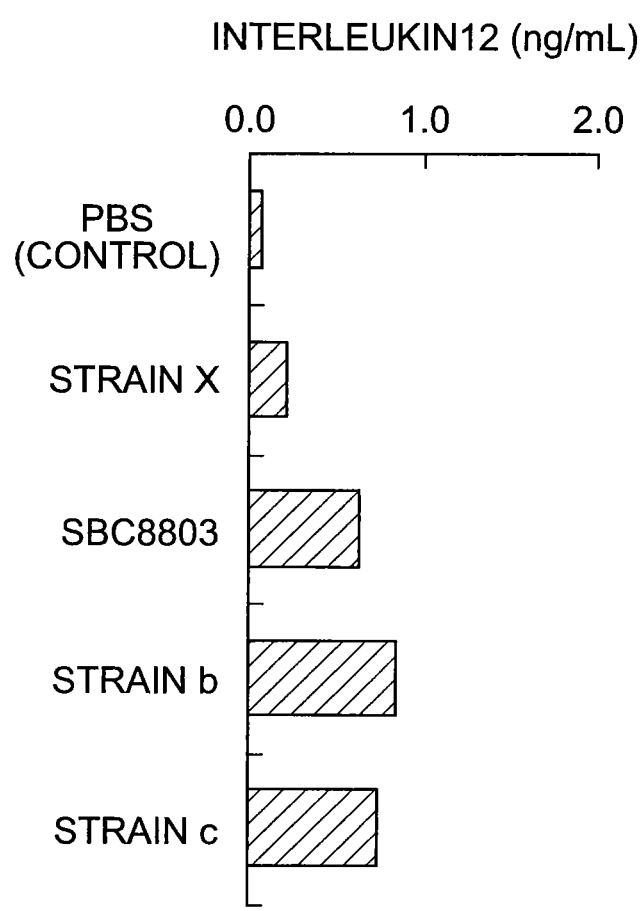
FIG. 3 shows the amount of interleukin 12 produced by spleen cells of OVA-immunized mice upon addition of OVA and a cell suspension of each of bacterial strains.
Figure 4:
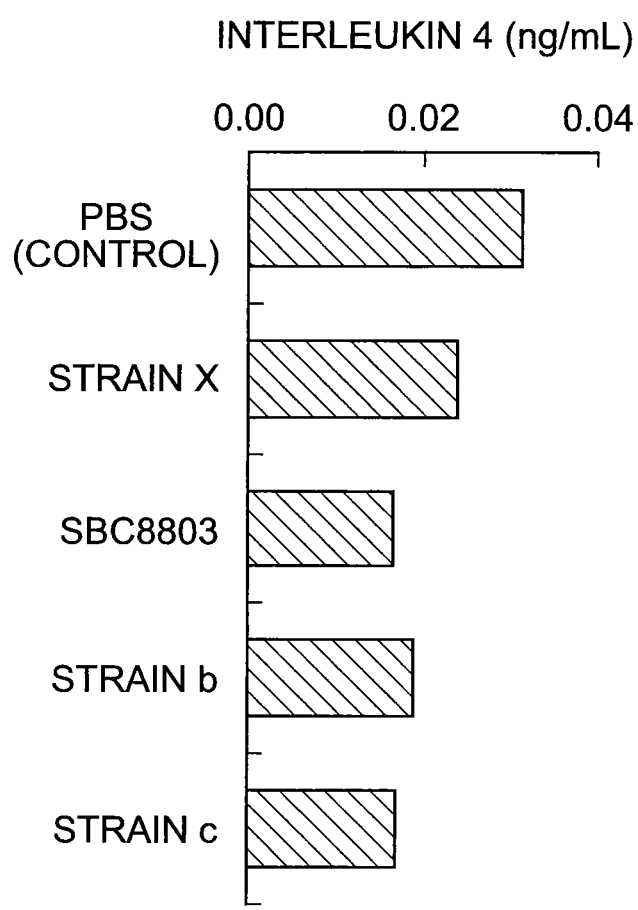
FIG. 4 shows the amount of interleukin 4 produced by spleen cells of OVA-immunized mice upon addition of OVA and a cell suspension of each of bacterial strains.
Figure 5:
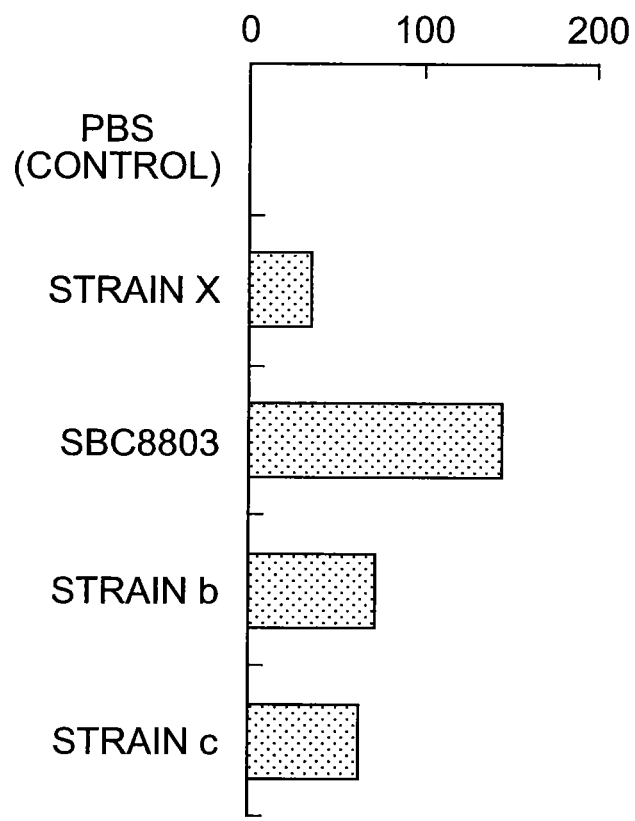
FIG. 5 is a graph showing the interferon γ/interleukin 4 ratio calculated as an index of the Th1/Th2 balance of spleen cells of OVA-immunized mice.

FIG. 2 shows the amount of interferon γ produced by spleen cells of OVA-immunized mice upon addition of OVA and a cell suspension of each bacterial strain. FIG. 3 shows the amount of interleukin 12 produced by spleen cells of OVA-immunized mice upon addition of OVA and a cell suspension of each bacterial strain. FIG. 4 shows the amount of interleukin 4 produced by spleen cells of OVA-immunized mice upon addition of OVA and a cell suspension of each bacterial strain. FIG. 5 is a graph showing the interferon γ/interleukin 4 ratio calculated as an index of the Th1/Th2 balance. Almost no production of the Th1 cytokines interferon γ and interleukin 12 occurred in the control in which OVA and PBS had been added, but the production of the Th2 cytokine interleukin 4 was prominently induced. This indicated that in the spleen cells of OVA-immunized mice, the Th1/Th2 balance was shifted toward Th2, thus promoting allergic reactions.

On the other hand, in the treatment group in which OVA and a cell suspension of SBC8803 had been added and the treatment group in which OVA and a cell suspension of strain b or c had been added, the production of the Th1 cytokines interferon γ and interleukin 12 was promoted compared to control and strain X belonging to Lactobacillus rhamnosus, and the production of the Th2 cytokine interleukin 4 was notably inhibited. The activity of SBC8803 was prominent compared to strains b and c, and was such that the Th1/Th2 balance of the spleen cells of OVA-immunized mice was largely shifted toward Th1. These results indicated that SBC8803 has potent antiallergic activity.

(Measurement of Total IgE and OVA-Specific IgE by ELISA)

As for measurement of total IgE, $2.5 \times 10^5$ spleen cells of OVA-immunized mice were seeded in a 96-well plate (cell density: $2.5 \times 10^6$ cells/mL), and cultured in RPMI 1640 medium containing 10% FBS under conditions of 37° C., 5% $CO_2$. OVA (final concentration: 100 μg/mL) and a cell suspension of each bacterial strain (final concentration: 1 μg/mL) were added to each well in which the spleen cells of OVA-immunized mice were being cultured. After 14 days, total IgE secreted into the culture supernatant was quantified by ELISA. As a control, PBS was added instead of the cell suspension, and quantification by ELISA was carried out in the same manner.

As for measurement of OVA-specific IgE, $2.5 \times 10^6$ spleen cells were seeded in a 48-well plate (cell density: $2.5 \times 10^6$ cells/mL), and cultured in RPMI 1640 medium containing 10% FBS under conditions of 37° C., 5% $CO_2$. OVA (final concentration: 100 μg/mL) and a cell suspension of each bacterial strain (final concentration: 1 μg/mL) were added to the spleen cells. After 3 days of cultivation, the spleen cells were washed 3 times with fresh medium to remove the OVA, and a cell suspension of each bacterial strain was again added to the washed spleen cells to bring the concentration to 1 μg/mL. After 11 days of cultivation, IgE secreted into the culture supernatant was quantified by ELISA. This quantification can be regarded as quantification of OVA-specific IgE. As a control, PBS was added instead of the cell suspension, and quantification by ELISA was carried out in the same manner.

Quantification of total IgE and OVA-specific IgE by ELISA was carried out as follows. First, 50 μL of anti-mouse IgE antibody (Mouse IgE ELISA Quantitation Kit, Bethyl Laboratories) prepared to 10 μg/mL was added to each well of a 96-well plate (Maxisorp Immunoplate, Nunk), and the mixture was allowed to stand overnight at 4° C. for fixation. Then, the 96-well plate was washed 3 times with wash buffer and subjected to blocking with 1% bovine serum albumin (BSA) (Sigma). Next, 50 μL of each culture supernatant or an IgE standard with a known concentration of IgE was added to each well and allowed to react with the anti-mouse IgE antibody for 90 minutes. After washing 3 times with wash buffer, 50 μL of biotinylated OVA prepared with Biotinylation Kit (Cygnus Technologies) was added to each well and allowed to react at room temperature for 90 minutes. Then, each well was washed 5 times with wash buffer, and streptavidin-HRP (BioSource) was added and allowed to react. After washing another 5 times with wash buffer, a TMB (tetramethylbenzidine) substrate solution (3,3',5,5'-Tetramethylbenzidine (TMB) Liquid Substrate System, Sigma) was added and allowed to react. After sufficient color development, 50 μL of 2N sulfuric acid was added to each well to terminate the reaction, and the absorbance at 450 nm was measured. A standard curve was prepared from the absorbances of the IgE standards, and IgE produced by the OVA mouse spleen cells was quantified using the standard curve. The amount of OVA-specific IgE was expressed as a value relative to the absorbance of the control (negative control), due to the lack of an OVA-specific IgE standard.

Figure 6:
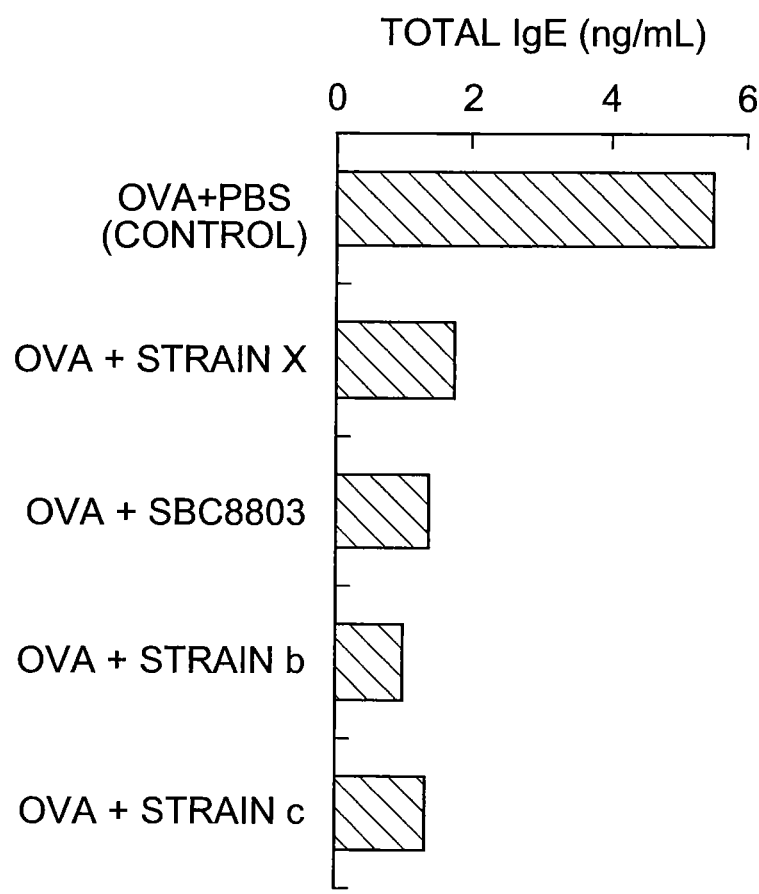
FIG. 6 shows the effect of a cell suspension of each of bacterial strains on total IgE production by spleen cells of OVA-immunized mice which is induced by addition of OVA.
Figure 7:
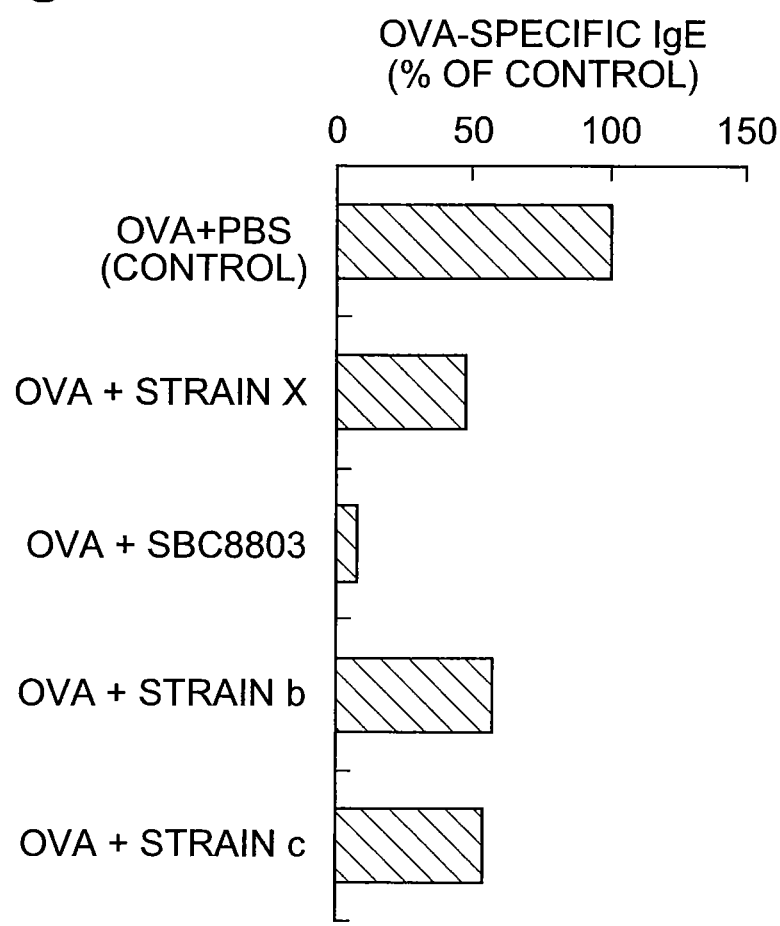
FIG. 7 shows the effect of a cell suspension of each of bacterial strains on OVA-specific IgE production by spleen cells of OVA-immunized mice which is induced by addition of OVA.

FIG. 6 shows the effect of a cell suspension of each bacterial strain on total IgE production by spleen cells of OVA-immunized mice which is induced by addition of OVA. FIG. 7 shows the effect of a cell suspension of each bacterial strain on OVA-specific IgE production by spleen cells of OVA-immunized mice which is induced by addition of OVA.

Addition of a cell suspension of SBC8803 inhibited OVA-induced production of total IgE and OVA-specific IgE by about 75% and 95%, respectively.

On the other hand, strains b and c and strain X belonging to *Lactobacillus rhamnosus* exhibited weak activities compared to SBC8803, although they inhibited OVA-induced production of total IgE and OVA-specific IgE.

These results demonstrate that SBC8803 belonging to *Lactobacillus brevis* subspecies *brevis* has an interferon γ and interleukin 12 production-promoting effect and an IgE production-inhibiting effect, and that it exhibits more potent antiallergic activity compared to hitherto-known lactic acid bacteria strains.

iv) IgE Production-Inhibiting Effect of SBC8803 on OVA-Immunized Mice (In Vivo)

SBC8803, which had been shown to have potent antiallergic activity in the in vitro experiments, was evaluated in vivo with respect to its IgE production-inhibiting effect in OVA-immunized mice. Also, strain X belonging to *Lactobacillus rhamnosus* was examined in the same manner and compared with SBC8803.

OVA-immunized mice were prepared by primary and booster immunizations with OVA (ovalbumin, eggwhite, purified; Worthington Biochemical) in the same manner as described above. They were divided into 3 groups of 10 mice each based on body weight, and a cell suspension of SBC8803 or strain X or PBS (control) was administered intraperitoneally at 200 μL once every two days from one week before primary immunization to one week after booster immunization. Each cell suspension was prepared by suspending lyophilized bacterial cells in PBS to a final concentration of 1 mg/mL and subjecting the suspension to autoclave sterilization (121° C., 15 min) in the same manner as described above.

One week after the booster immunization, blood was sampled from the tail vein of each mouse, and the amounts of total IgE and OVA-specific IgE in the separated serum were measured by ELISA. Measurement of total IgE and OVA-specific IgE in the serum by ELISA was carried out by the same procedure as described above.

Figure 8:
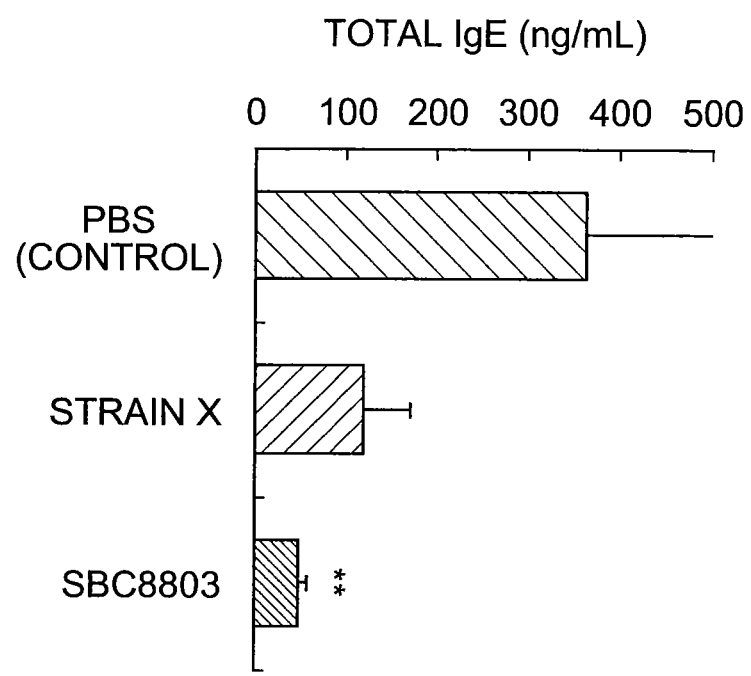
FIG. 8 shows the amount of total IgE secreted into the peripheral blood of OVA-immunized mice after intraperitoneal administration of each of bacterial strains.
Figure 9:
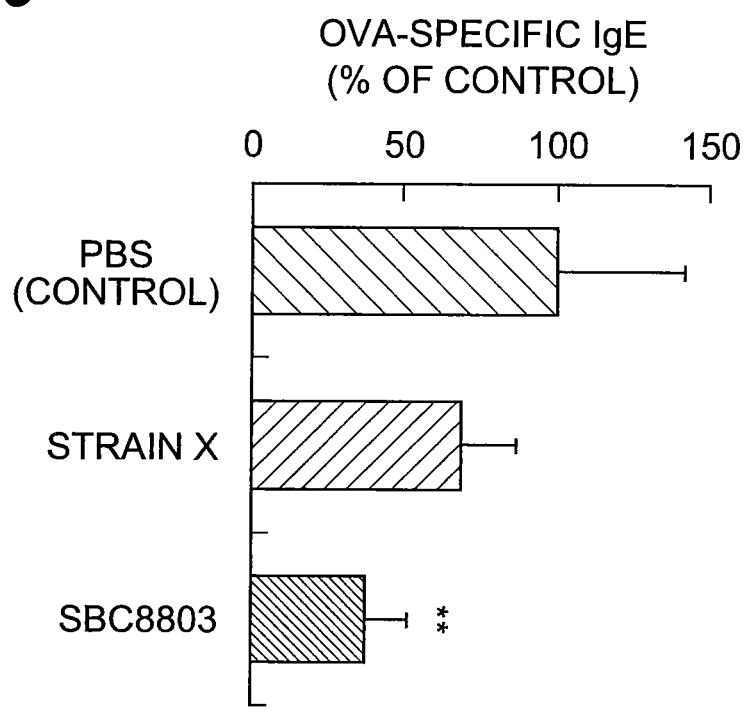
FIG. 9 shows the amount of OVA-specific IgE secreted into the peripheral blood of OVA-immunized mice after intraperitoneal administration of each of bacterial strains.

FIG. 8 shows the amount of total IgE secreted into the peripheral blood of OVA-immunized mice after intraperitoneal administration of each bacterial strain. FIG. 9 shows the amount of OVA-specific IgE secreted into the peripheral blood of OVA-immunized mice after intraperitoneal administration of each bacterial strain. The double asterisks (**) in the graphs indicate that the difference from control is statistically significant at $p<0.01$.

Addition of a cell suspension of SBC8803 suppressed total IgE secreted into the peripheral blood of OVA mice by about 85% and suppressed OVA-specific IgE by about 60%. This effect was statistically significant compared to the control in which PBS had been administered.

On the other hand, strain X belonging to *Lactobacillus rhamnosus* exhibited a weak activity compared to SBC8803 and its effect was not statistically significant compared to control, although it suppressed total IgE and OVA-specific IgE secreted into the peripheral blood of OVA mice.

These results demonstrate that SBC8803 belonging to *Lactobacillus brevis* subspecies *brevis* has an inhibitory effect on IgE production in vivo as well, and that it exhibits more potent antiallergic activity compared to hitherto-known lactic acid bacteria strains.

v) Effect of SBC8803 on Atopic Dermatitis (In Vivo)

NC/Nga mice are disease model mice in which application of 2,4,6-trinitrochlorobenzene (picryl chloride) induces atopic dermatitis, and it has been reported that elevation of serum IgE antibody levels in NC/Nga mice correlates with the onset of atopic dermatitis. The effect of oral administration of SBC8803 on the onset of atopic dermatitis in the NC/Nga mice was examined by applying picryl chloride while feeding NC/Nga mice a mixed diet containing 0.05% or 0.5% SBC8803.

(Induction of Atopic Dermatitis in NC/Nga Mice)

Eight-week-old NC/Nga mice (male) were divided into 3 groups of 10 mice each based on body weight, and 150 μL of a 5% picryl chloride solution (in an ethanol/acetone mixture (4:1)) was applied to the shaven abdominal area and footpads of each mouse as a primary sensitization. From 4 days thereafter, a solution of 1% picryl chloride in olive oil was applied to both auricles at 15 μL once a week (total: 9 times) as a secondary sensitization, inducing the onset of atopic dermatitis in the NC/Nga mice.

(Oral Administration of SBC8803)

NC/Nga mice of each group were freely fed a control diet containing no SBC8803, a mixed diet containing 0.05% SBC8803 or a mixed diet containing 0.5% SBC8803 from 2 weeks before the primary sensitization to the end of the test.

After the primary sensitization, the dermatitis scores, ear thicknesses and serum IgE antibody levels of NC/Nga mice of each group were measured over time, and the average values were determined and compared between the groups. The dermatitis scores were measured by the method of Matsuda et al. (Matsuda et al., Int. Immunol., 1997, Vol. 9, p. 461-466). Specifically, the extents of redness, hemorrhage, edema, alopecia, skin loss and rash were examined and scored on a scale of 0 to 3, with 0 representing lack of symptoms, 1 representing mild symptoms, 2 representing moderate symptoms and 3 representing serious symptoms. The ear thicknesses were measured using a dial thickness gauge (Mitsutoyo). The serum IgE antibody levels were measured by sandwich ELISA mentioned above.

Figure 10:
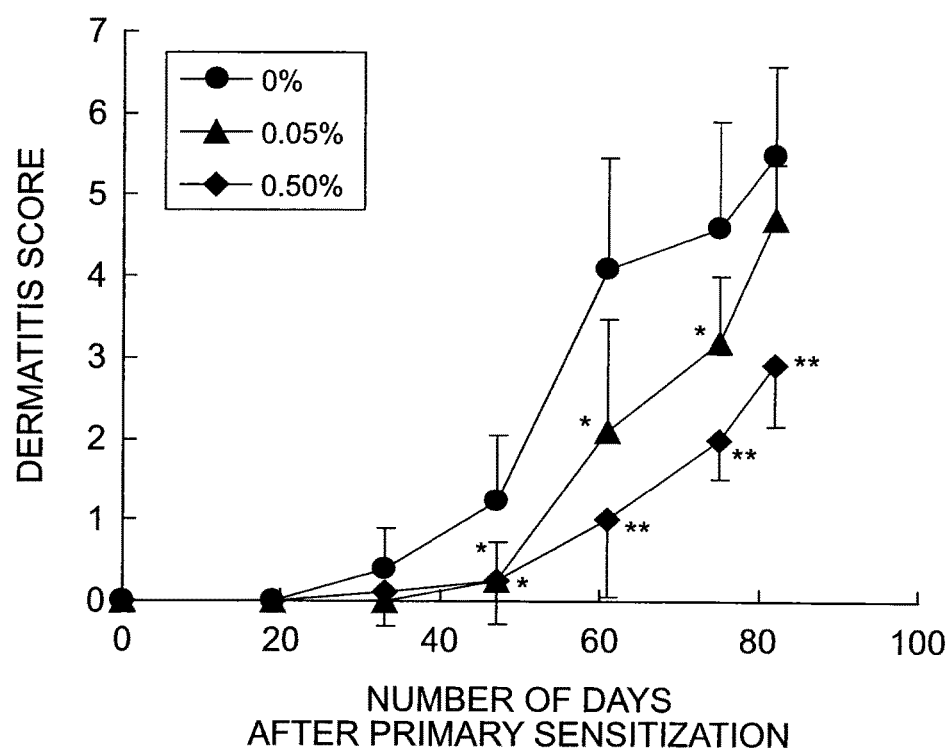
FIG. 10 shows the time-dependent changes in dermatitis score of NC/Nga mice fed a mixed diet containing SBC8803.

FIG. 10 shows the time-dependent changes in dermatitis score of NC/Nga mice fed a mixed diet containing SBC8803. The single asterisks (*) in the graph indicate that the difference from the NC/Nga mice fed the control diet is statistically significant at $p<0.05$, and the double asterisks (**) indicate that the difference from the NC/Nga mice fed the control diet is statistically significant at $p<0.01$.

Increase in dermatitis score was notably suppressed in the NC/Nga mice fed the mixed diet containing 0.05% or 0.5% SBC8803. This effect was statistically significant compared to the NC/Nga mice fed the control diet.

Figure 11:
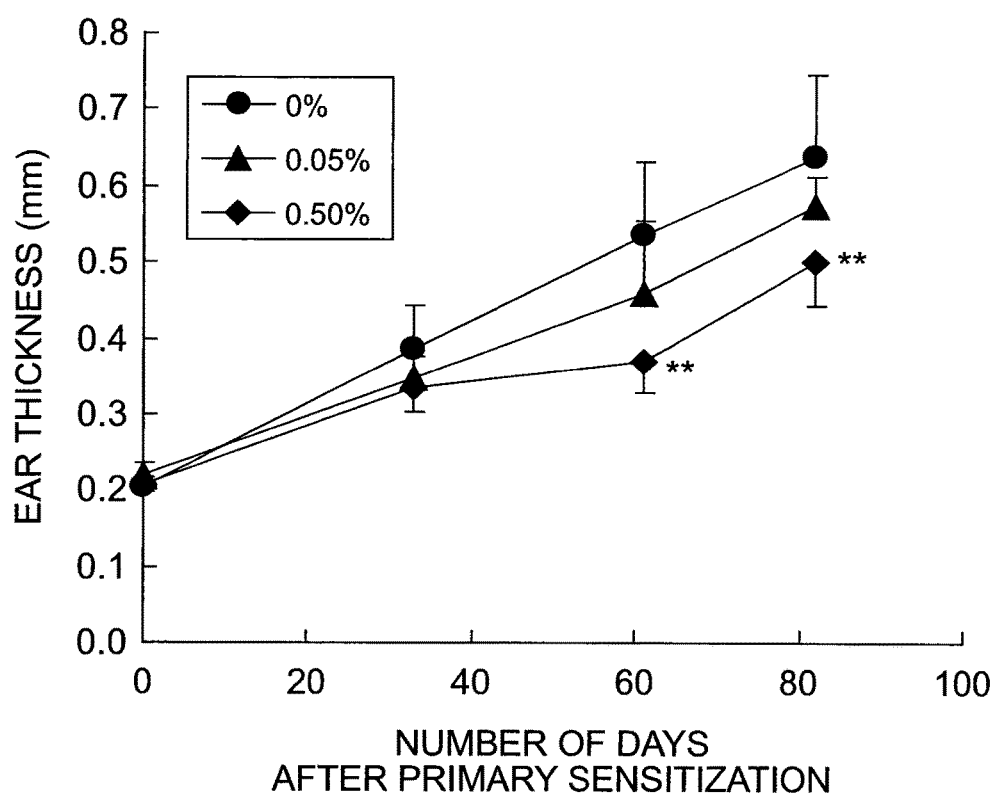
FIG. 11 shows the time-dependent changes in ear thickness of NC/Nga mice fed a mixed diet containing SBC8803.

FIG. 11 shows the time-dependent changes in ear thickness of NC/Nga mice fed a mixed diet containing SBC8803. The double asterisks (**) in the graph indicate that the difference from the NC/Nga mice fed the control diet is statistically significant at p<0.01.

Increase in ear thickness was notably suppressed in the NC/Nga mice fed the mixed diet containing 0.5% SBC8803. This effect was statistically significant compared to the NC/Nga mice fed the control diet.

Figure 12:
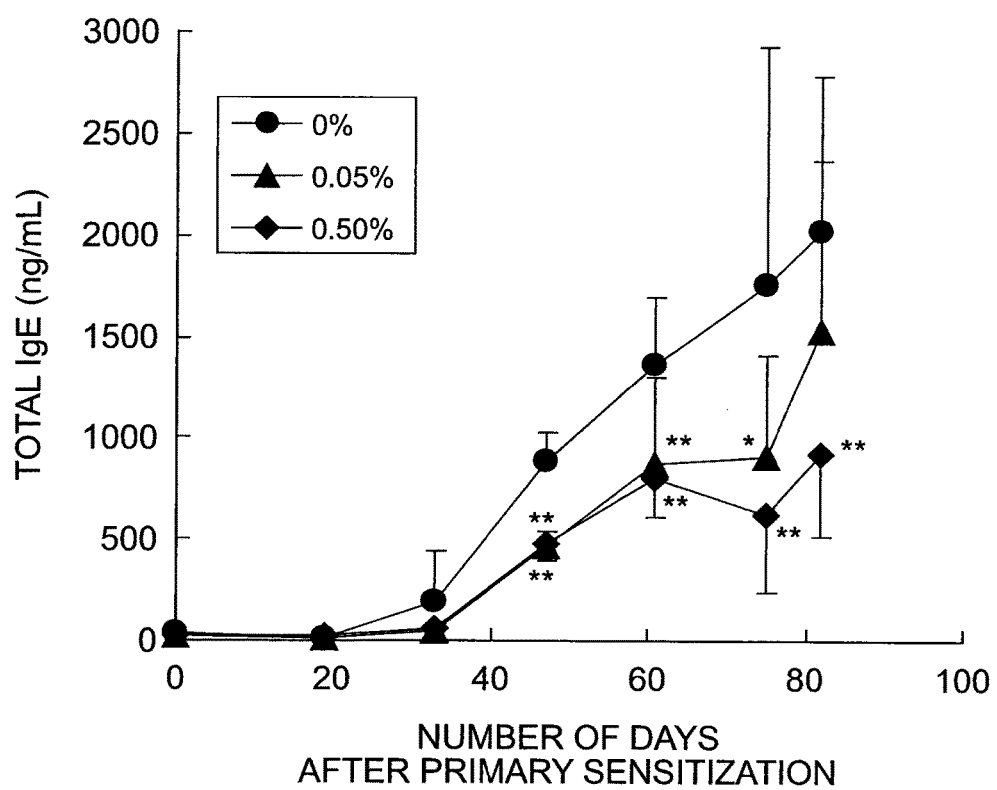
FIG. 12 shows the time-dependent changes in serum IgE antibody level of NC/Nga mice fed a mixed diet containing SBC8803.

FIG. 12 shows the time-dependent changes in serum IgE antibody level of NC/Nga mice fed a mixed diet containing SBC8803. The single asterisks (*) in the graph indicate that the difference from the NC/Nga mice fed the control diet is statistically significant at p<0.05, and the double asterisks (**) indicate that the difference from the NC/Nga mice fed the control diet is statistically significant at p<0.01.

Increase in serum IgE antibody level was notably suppressed in the NC/Nga mice fed the mixed diet containing 0.05% or 0.5% SBC8803. This effect was statistically significant compared to the mice fed the control diet.

These results demonstrate that SBC8803 belonging to *Lactobacillus brevis* subspecies *brevis* has an inhibitory effect on the onset of atopic dermatitis, and exhibits potent antiallergic activity.

4) Measurement of Ability to Produce γ-Aminobutyric Acid (GABA)

The ability of SBC8803 belonging to *Lactobacillus brevis* subspecies *brevis* to produce γ-aminobutyric acid (GABA) was examined. First, SBC8803 was inoculated into 100 mL of liquid medium (3% malt extract (Difco), 2% yeast extract (Difco), 0.2% sodium glutamate, pH 6.0) and cultured statically for 4 days. Then, the culture solution of SBC8803 was centrifuged at 1500 rpm for 10 minutes and the culture supernatant was recovered. GABA contained in the culture supernatant was quantified by HPLC. The HPLC conditions were as follows:

HPLC apparatus: Agilent HPLC 1100;
Column: ZORBAX eclipse AAA (4.6×150 mm, 3.5 μm) (Shimadzu GLC);
Column oven: 40° C.;
Flow rate: 1.0 mL/min;
Fluorescence detector: Ex. 340 nm, Em. 450 nm;
HPLC reagent: 10 mg/mL Agilent OPA reagent (0.4 M borate buffer, pH 10.2) (Shimadzu GLC);
Eluents: Solvent A: 40 mM $NaH_2PO_4$ (pH 7.8); Solvent B: 45 vol % acetonitrile, 45 vol % MeOH, 10% $H_2O$;
Timetable (gradient): See Table 1.

TABLE 1

| Time (min) | Solvent A | Solvent B |
|---|---|---|
| 0.0 | 90% | 10% |
| 4.0 | 90% | 10% |
| 20.0 | 65% | 35% |
| 25.0 | 10% | 90% |
| 35.0 | 10% | 90% |
| 36.0 | 90% | 10% |
| 46.0 | 90% | 10% |

SBC8803 produced 102.5 μmol/L of GABA in the culture supernatant.

These results demonstrate that SBC8803 belonging to *Lactobacillus brevis* subspecies *brevis* is a bacterial strain that is capable of growing in effervescent alcoholic beverages, has potent antiallergic activity and produces GABA which exhibits anti-stress activity.

5) Sensory Evaluation of Lactic Acid-Fermented Fruit Juice Produced Using SBC8803

Lactic acid-fermented fruit juice was produced using SBC8803 having antiallergic activity, and sensory evaluation of aroma and taste was performed on the lactic acid-fermented fruit juice.

Table 2 shows the type of fruit, sugar content and pH of each juice used for the lactic acid fermentation.

TABLE 2

| Juice name | Type of fruit | Sugar content | pH |
|---|---|---|---|
| GF-10 | Grapefruit | Bri × 10 | 5.0 |
| GF-20 | Grapefruit | Bri × 20 | 5.0 |
| AP-10 | Apple | Bri × 10 | 5.0 |
| AP-20 | Apple | Bri × 20 | 5.0 |
| WG-10 | White grape | Bri × 10 | 5.0 |
| LE-5 | Lemon | Bri × 5 | 5.0 |

Each juice was prepared by diluting grapefruit juice concentrate, apple juice concentrate, white grape juice concentrate or lemon juice concentrate with sterile water to the prescribed sugar content, and adjusting the pH by addition of NaOH. As for the lactic acid fermentation, $1 \times 10^9$ cells of SBC8803 were inoculated into 100 mL of each juice, and the mixture was allowed to stand at 30° C. for 72 hours, stirring once a day. Upon completion of the fermentation, the turbidity of each lactic acid-fermented juice was measured with a spectrophotometer (Taitec) and the lactic acid content was measured with an F-kit D-/L-lactic acid (J. K. International). The turbidity was used as an index of the extent of SBC8803 proliferation, and the lactic acid content was used as an index of the extent of lactic acid fermentation.

Table 3 shows the turbidity, lactic acid content and sensory evaluation results for each lactic acid-fermented juice.

TABLE 3

| | GF-10 | GF-20 | AP-10 | AP-20 |
|---|---|---|---|---|
| Turbidity (OD 660 nm) | 0.04 | 0.06 | 0.07 | 0.13 |
| D-Lactic acid (g/L) | 0.75 | 0.12 | 0.35 | 0.67 |
| L-Lactic acid (g/L) | 0.84 | 0.19 | 1.17 | 2.12 |
| Sensory evaluation results | Maintained original juice's flavor | Maintained original juice's flavor | Maintained original juice's flavor; gentle aroma; fresh acidity | Maintained original juice's flavor; gentle aroma; fresh acidity |

| | WG-10 | LE-5 |
|---|---|---|
| Turbidity (OD 660 nm) | 0.04 | 0.01 |
| D-Lactic acid (g/L) | 0.16 | 0.20 |
| L-Lactic acid (g/L) | 0.57 | 0.56 |
| Sensory evaluation results | Maintained original juice's flavor | Maintained original juice's flavor |

As for any juice used in this experiment, lactic acid fermentation by SBC8803 proceeded to produce a lactic acid-fermented fruit juice having no yogurt flavor and retaining the flavor of the original juice. In particular, the fermentation using apple juice further yielded a gentle aroma and fresh acidity, which are desirable properties for a lactic acid-fermented beverage.

INDUSTRIAL APPLICABILITY

The bacterial strain of the invention is capable of growing in effervescent alcoholic beverages, and this property can be utilized to separate the bacterial strain of the invention from other lactic acid bacteria strains with no antiallergic activity. Also, since the bacterial strain of the invention produces γ-aminobutyric acid (GABA), it has anti-stress activity as well as antiallergic activity, and is therefore expected to have a robust effect in the prevention and treatment of allergic diseases which correlate with physical and psychological stress. The present invention further provides highly safe beverages, foods and antiallergic agents which contain cells of the aforementioned bacterial strain and have antiallergic activity.

The invention claimed is:

1. A method of treating an allergy in a subject in need thereof, the method comprising administering to the subject a composition comprising a bacterial strain of SBC8803 (FERM BP-10632) belonging to *Lactobacillus brevis* subspecies *brevis*.

2. The method of claim 1, wherein the composition is a food.

3. The method of claim 1, wherein the composition is a fruit juice.

4. The method of claim 1, wherein the administering is performed by oral administration.

5. The method of claim 1, wherein the allergy is food allergy.

6. The method of claim 1, wherein the composition further comprises at least one additive selected from the group consisting of apple fiber, soybean fiber, meat extract, black vinegar extract, gelatin, corn starch, honey, animal and vegetable oil and fat, monosaccharides, disaccharides, polysaccharides, sugar alcohols, and vitamins.

7. The method of claim 1, wherein the composition further comprises at least one additive selected from the group consisting of glucose, sucrose, fructose, mannitol, dextrose, starch, erythritol, xylitol, sorbitol, and vitamin C.

8. The method of claim 1, wherein the composition further comprises at least one pharmaceutically acceptable additive selected from the group consisting of monosaccharides, disaccharides, polysaccharides, sugar alcohols, vitamins, acacia gum, calcium phosphate, alginates, calcium silicate, microcrystalline cellulose, polyvinylpyrrolidone, cellulose derivatives, tragacanth, gelatin, syrups, methyl hydroxybenzoate, talc, magnesium stearate, water, and mineral oils.

9. The method of claim 1, wherein the composition excludes steroid.

10. The method of claim 1, wherein the composition is a beverage.

11. The method of claim 10, wherein the beverage is an effervescent beverage.

12. The method of claim 11, wherein the effervescent beverage is beer.

* * * * *